(12) United States Patent
Honma et al.

(10) Patent No.: US 8,647,664 B2
(45) Date of Patent: Feb. 11, 2014

(54) ADHESIVE PREPARATION

(75) Inventors: Sachiko Honma, Tsukuba (JP); Tetsuro Tateishi, Tsukuba (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 737 days.

(21) Appl. No.: 12/309,226

(22) PCT Filed: Jun. 27, 2007

(86) PCT No.: PCT/JP2007/062906
§ 371 (c)(1),
(2), (4) Date: Feb. 20, 2009

(87) PCT Pub. No.: WO2008/007554
PCT Pub. Date: Jan. 17, 2008

(65) Prior Publication Data
US 2009/0246263 A1    Oct. 1, 2009

(30) Foreign Application Priority Data

Jul. 14, 2006    (JP) ................................ P2006-194624

(51) Int. Cl.
*A61F 13/02* (2006.01)
*A61L 15/16* (2006.01)
*A61F 13/00* (2006.01)
*A61K 31/445* (2006.01)

(52) U.S. Cl.
USPC ............ 424/448; 424/449; 424/447; 514/329

(58) Field of Classification Search
USPC ............................ 424/448, 449, 447; 514/329
See application file for complete search history.

(56) References Cited

U.S. PATENT DOCUMENTS

| | | | |
|---|---|---|---|
| 4,588,580 A | 5/1986 | Gale et al. | |
| 5,656,286 A * | 8/1997 | Miranda et al. | 424/449 |
| 6,791,003 B1 | 9/2004 | Choi et al. | |
| 7,718,188 B2 | 5/2010 | Ito et al. | |
| 2006/0034900 A1 | 2/2006 | Saeki et al. | |
| 2006/0078603 A1* | 4/2006 | Nguyen | 424/449 |
| 2006/0078604 A1 | 4/2006 | Kanios et al. | |

FOREIGN PATENT DOCUMENTS

| | | |
|---|---|---|
| JP | 9511987 | 12/1997 |
| JP | 10045570 | 2/1998 |
| JP | 2000044476 | 2/2000 |
| JP | 2006513160 | 4/2006 |
| KR | 20010036685 | 5/2001 |
| KR | 100391229 | 11/2003 |
| KR | 20050062627 | 6/2005 |
| KR | 20060049296 | 5/2006 |
| TW | 200413034 | 8/2004 |
| WO | 93/00058 A1 | 1/1993 |
| WO | 2004/017941 A2 | 3/2004 |
| WO | WO 2004/035054 A1 | 4/2004 |
| WO | 2004/098567 A2 | 11/2004 |
| WO | 2005/123046 A1 | 12/2005 |

OTHER PUBLICATIONS

Translation of International Preliminary Report on Patentability, Forms PCT/IB/373, PCT/IB338, PCT/ISA237, 7 pgs., Int. Bureau of WIPO, Geneva, Switzerland, Jan. 29, 2009.
European Search Report for counterpart application EP07767707.8; mailed on Sep. 6, 2012.
Subbu Venkatraman, et al., "Skin adhesives and skin adhesion—1. Transdermal drug delivery systems", Biomaterials, Elsevier Science Publishers BV., Barking, GB, vol. 19, No. 13, Jun. 1, 1998, p. 1119-1136, XP004161374.
Office Action in counterpart to TW Patent Application No. 096125256 dated May 16, 2013, 7 pages.

* cited by examiner

*Primary Examiner* — Abigail Fisher
(74) *Attorney, Agent, or Firm* — Nath, Goldberg & Meyer; Sheldon M. McGee

(57) ABSTRACT

A patch preparation having a backing layer and a drug layer laminated on the backing layer; wherein the drug layer contains an adhesive containing at least one compound selected from the group consisting of fentanyl and pharmaceutically acceptable salts thereof, polyisobutylene, and a silicon-containing polymer; and a mass ratio of the polyisobutylene and the silicon-containing polymer in the adhesive is 20:1 to 7:3.

15 Claims, 1 Drawing Sheet

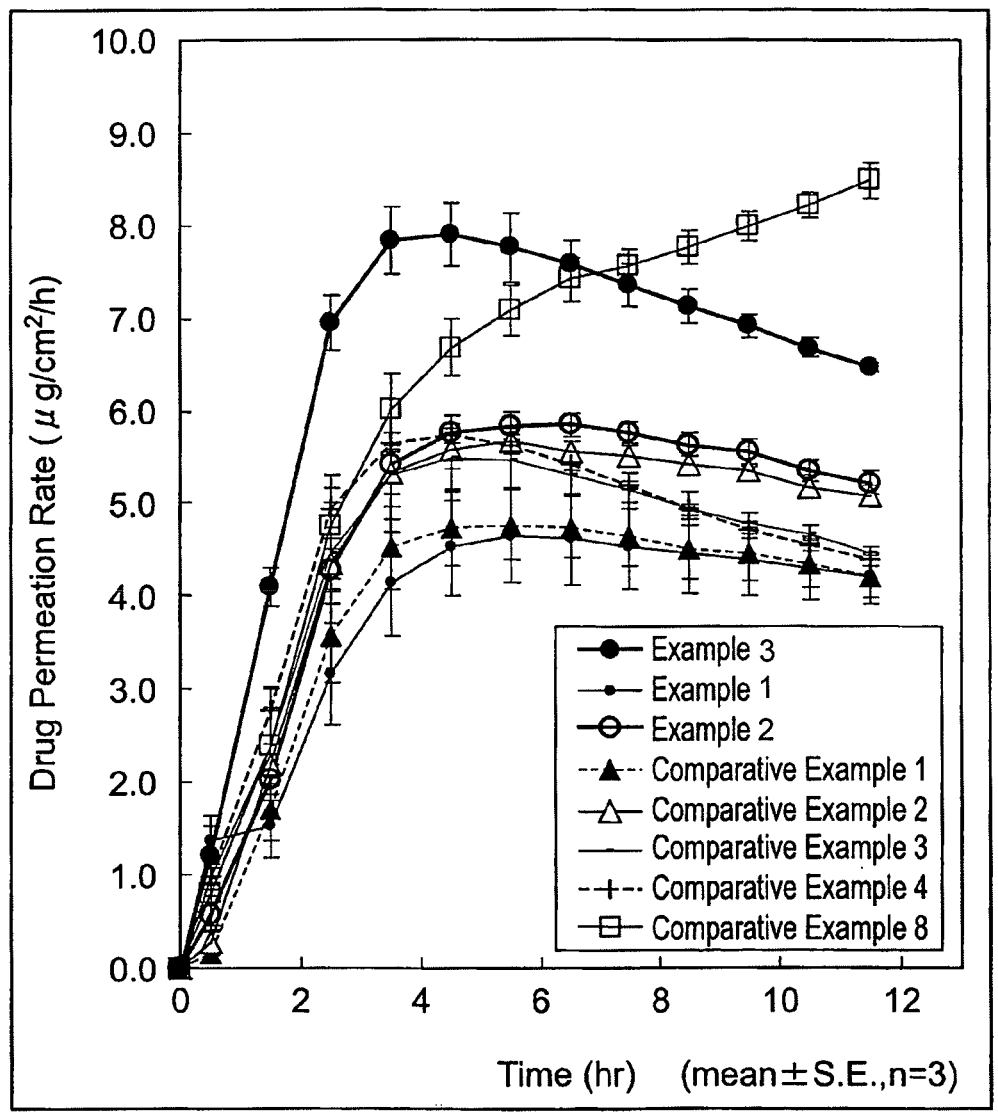

ADHESIVE PREPARATION

TECHNICAL FIELD

The present invention relates to a patch preparation and more particularly, to a patch preparation containing fentanyl and/or a pharmaceutically acceptable salt thereof as an active ingredient.

BACKGROUND ART

Fentanyl, a selective μ-opioid agonist, is an analgesic or anesthetic adjunct. Lately, the palliative treatment of cancer pains has particularly progressed, and fentanyl has been establishing a secure status as an opioid drug alternative to morphine. Further, when QOL (quality of life) of a patient with cancer pains is considered, transdermal administration is one of the most convenient routes.

One of the preferred embodiments of the transdermal administration is to use a patch preparation wherein a drug layer (containing a drug and a pressure-sensitive adhesive), formed on a backing layer, is covered with a release liner. In general, when a drug is transdermally administered using a patch preparation, it is desirable that a drug be dissolved in an adhesive in view of its diffusion and skin permeation. Further, to secure a predetermined amount of a drug to be absorbed, it is desirable to mix a transdermal absorption enhancer in a pressure-sensitive adhesive.

Thus, it is common for a pressure-sensitive adhesive to contain liquid ingredients such as solubilizers, solubilizing adjuvants, transdermal absorption enhancers, and the like. However, containing such ingredients posed a problem in that the cohesive force of an adhesive base was reduced. When the cohesive force of an adhesive base is reduced, the skin permeability of a drug tends to be also reduced. For this reason, if liquid ingredients in a pressure-sensitive adhesive are increased for the purpose of enhancing the diffusion and skin permeation of a drug, it may, on the contrary, deteriorate the skin permeability of the drug.

Generally, basic drugs such as fentanyl have low skin permeability. Due to this property, when fentanyl is contained in a pressure-sensitive adhesive, it is imperative to add a large amount of liquid ingredients in the pressure-sensitive adhesive to attain adequate drug diffusion and skin permeation. However, since a large amount of liquid ingredients added causes reduced cohesive force of an adhesive base due to the reason described above, it raised a problem that sufficient skin permeability of a drug could not be achieved.

To solve the above problem, fentanyl-containing patch preparations are disclosed in Patent Documents 1 to 4. More specifically, known patch preparations include; patch preparations in reservoir formulation and multilaminate formulation (Patent Document 1), a patch preparation containing an organic acid salt, a styrene-isoprene-styrene block copolymer and polyisobutylene (Patent Document 2), a patch preparation containing N-methyl-2-pyrrolidone (Patent Document 3), and a patch preparation in which fentanyl particles are suspended in more than 1 solvated silicone-based pressure-sensitive adhesive (Patent Document 4).

Patent Document 1: Japanese Patent Laid-Open No. 61-37725
Patent Document 2: Japanese Patent Laid-Open No. 10-45570
Patent Document 3: Japanese patent Laid-Open No. 2000-44476
Patent Document 4: Japanese Patent Application (International application) Laid-Open No. 2006-513160

DISCLOSURE OF THE INVENTION

Problems to be Solved by the Invention

However, the abovementioned known fentanyl-containing patch preparations had the following drawbacks.

More specifically, the fentanyl-containing reservoir patch preparation disclosed in Patent Document 1 has a drug reservoir layer in which a drug is enclosed in a solution or semi-solid form. For this reason, it requires highly precisional manufacturing processes to prevent the drug from volatilization and leakage. Further, since such a reservoir patch preparation structurally requires a drug release rate-controlling membrane, the number of parts composing a patch preparation increases, etc., thereby posing a problem by complicating the manufacturing process.

Further, the fentanyl-containing multilaminate patch preparation disclosed in Patent Document 1 requires to contain a large amount (e.g., 10 to 30%) of fentanyl in a pressure-sensitive adhesive, wherein the fentanyl is likely to be crystallized over time, causing an undesirable problem from the viewpoints of adhesion and drug release.

The fentanyl-containing patch preparations disclosed in Patent Documents 2 and 3 require a number of restrictions in conditions of manufacturing processes (pulverizing, mixing, film forming, and drying), complicating the production method which is problematic. Further, the fentanyl-containing patch preparation disclosed in Patent Document 3 had high drug releasability or absorption, thereby causing a problem in that the drug tends to quickly deplete when applied. Furthermore, the fentanyl-containing patch preparation of Patent Document 3 had a problem of the so-called "sticking-out".

More specifically, the patch preparation is typically packaged individually in a water impermeable packaging material to prevent the contained drug from being volatilized or affected by humidity. However, such an individually packaged patch preparation had the so-called "sticking-out" problem, which causes a pressure-sensitive adhesive to protrude from the edge of a patch preparation and stick to the inner surface of the packaging material or a pressure-sensitive adhesive to extend behind the backing layer, making it difficult to take the patch preparation for use. In particular, when the pressure-sensitive adhesive contains a plasticizer, tackifier, solubilizer, etc., these agents stick out from the edge of the drug layer and attach (extend) to the back of the backing layer or release liner, even to the inner surface of the packaging material. Consequently, the patch preparation adheres to the inner surface of the packaging material, making it difficult to take the patch preparation.

The fentanyl-containing patch preparation disclosed in Patent Document 4 posed problems such as low adhesion, poor peeling of the release liner.

The present invention has accomplished in the light of the circumstances described above. An object of the present invention is to provide a fentanyl-containing patch preparation that is manufactured easily, prevented sufficiently from the sticking-out and crystal formation, and imparted good drug permeability through the skin.

Means for Solving the Problems

The present inventors have conducted extensive studies, and found that the above object is achieved by a patch preparation comprising a backing layer and a drug layer laminated on the backing layer, wherein the drug layer consists of a pressure-sensitive adhesive comprising polyisobutylene, a silicon-containing polymer and at least one compound selected from the group consisting of fentanyl and pharmaceutically acceptable salts thereof, and a mass ratio of the polyisobutylene and the silicon-containing polymer in the pressure-sensitive adhesive is 20:1 to 7:3.

Such a fentanyl-containing patch preparation is easily manufactured, sufficiently prevented from the sticking-out and crystal formation, and imparted good skin permeability. The reason rendering these effects is yet to be discovered. However, it is presumably at least due to the use of a mixture of polyisobutylene and a silicon-containing polymer as a pressure-sensitive adhesive substance (hereinafter sometimes referred to as "adhesive base") in which fentanyl is to be contained and also set the mass ratio for such a mixture within the specified range.

Further, the patch preparation having the above structure requires a small number of parts for the manufacture and is less restrictive in manufacturing process conditions, thereby providing an effect that manufacturing process is easier than those for known patch preparations.

Furthermore, the conventional fentanyl-containing patch preparations are likely to leave the pressure-sensitive adhesive on the skin (hereinafter referred to as "adhesive remnant") when a patch preparation is detached from the skin, imposing a burden to a patient. However, according to the fentanyl-containing patch preparation of the present invention, the adhesive remnant can be sufficiently prevented.

It is preferred that the abovementioned polyisobutylene comprises a high molecular weight polyisobutylene having an average molecular weight of 800,000 to 1,600,000 and a low molecular weight polyisobutylene having an average molecular weight of 30,000 to 80,000. The adhesion of the patch preparation can be hence improved.

It is preferred that the silicon-containing polymer described above be a polymer having an organopolysiloxane skeleton (preferably an organopolysiloxane skeleton) or a composition containing such a polymer. Preferred polymers having an organopolysiloxane skeleton have hydroxyl groups thereof at least partially capped by a trimethylsilyl group. The polymer having an organopolysiloxane skeleton wherein at least a part of its hydroxyl group is capped by a trimethylsilyl group has a small number of free silanol groups, and hence has a low interaction with a drug (e.g., chemical and physical bond), whereby the drug releasability tends to increase.

As described above, although the silicon-containing polymer may be a composition containing a polymer having an organopolysiloxane skeleton, it is preferable for the composition to be a pressure-sensitive composition. Such a composition does not deteriorate the adhesion of an adhesive constituting a drug layer and maintains good releasability of fentanyl or a pharmaceutically acceptable salt thereof.

Further, the pressure-sensitive adhesive preferably contains a transdermal absorption enhancer. The use of such an enhancer enables effective drug absorption to the skin.

Furthermore, the above transdermal absorption enhancer is preferably at least one compound selected from the group consisting of isopropyl myristate, isopropyl palmitate, sorbitan monooleate, oleyl alcohol, propylene glycol, dipropylene glycol, octyl dodecanol. The use of such an enhancer enables the drug skin permeability to be further improved.

The area of the drug layer to be contacted with the skin is preferably 5 to 50 $cm^2$.

Effects of the Invention

According to the present invention, the fentanyl-containing patch preparation, which is easily manufactured, sufficiently prevented from the sticking-out and crystal formation, and has good skin permeability, adhesion and tackiness to the skin, is provided. Further, according to the present fentanyl-containing patch preparation, the adhesive remnant is adequately prevented and the drug is absorbed for a longer time than the conventional fentanyl-containing patch preparations, thereby relieving the burden of patients.

BRIEF DESCRIPTION OF THE DRAWINGS

FIG. 1 is a graph showing changes over time in the drug permeability when the patch preparation of the present invention is applied to the skin.

BEST MODES FOR CARRYING OUT THE INVENTION

Preferred embodiments of the patch preparation according to the present invention are hereinafter described in detail. In the specification, "%" refers to "mass %", unless otherwise specified.

The patch preparation according to the present invention comprises a backing layer and a drug layer where drug layer consists of a specific adhesive and is laminated on the backing layer.

The pressure-sensitive adhesive comprises a drug having at least one activity (drug potency) selected from the group consisting of fentanyl and pharmaceutically acceptable salts thereof, and an adhesive base comprising polyisobutylene and a silicon-containing polymer.

The pressure-sensitive adhesive may contain, as an active drug, fentanyl and a pharmaceutically acceptable salt thereof independently or together as a mixture. However, it is preferable to contain fentanyl singly because an active drug has to be contained in the pressure-sensitive adhesive in a dissolved state.

The fentanyl content in the drug layer is preferably 1 to 6% based on the whole mass of the drug layer. A fentanyl content of 1% or more easily enables the patch preparation to deliver a sufficient drug permeation through the skin, and a fentanyl content of 6% or less can definitely eliminate adverse influence to the physical properties of the patch preparation caused by crystal formation. With a fentanyl content of 1 to 6%, a high blood level can be attained when the drug is transdermally administered. To prevent the adhesive remnant and crystal formation of the drug, the fentanyl content is more preferably 1 to 4%, and further more preferably 2 to 4%, based on the whole mass of the drug layer.

In view of the adhesion, it is preferred that the polyisobutylene comprises a high molecular weight polyisobutylene and a low molecular weight polyisobutylene. The viscosity average molecular weight (Staudinger) of the high molecular weight polyisobutylene is preferably 800,000 to 1,600,000, more preferably 900,000 to 1,500,000, and further preferably 1,000,000 to 1,400,000. The viscosity average molecular weight (Staudinger) of the low molecular weight polyisobutylene is preferably 30,000 to 80,000, more preferably 35,000 to 70,000, and further preferably 35,000 to 60,000. The above average molecular weights are viscosity average molecular weights (Staudinger) measured in accordance with a viscosity method.

Further, the mass ratio of the high molecular weight polyisobutylene to the low molecular weight polyisobutylene is preferably 1:9 to 2:3, and more preferably 1:7 to 1:3. By adjusting the mass ratio of the high molecular weight polyisobutylene to the low molecular weight polyisobutylene within the above range, the cohesion of the pressure-sensitive adhesive and adhesive remnant are definitely prevented.

Furthermore, the polyisobutylene content in the drug layer is preferably 40 to 94%, more preferably 50 to 90%, and further preferably 60 to 85%, based on the whole mass of the drug layer. When a polyisobutylene content is below 40%, sufficient adhesion may not be achieved, whereas when a polyisobutylene content exceeds 94%, the cohesion of the pressure-sensitive adhesive and adhesive remnant may be caused.

The silicon-containing polymer contained in the drug layer refers to polymers containing silicon in the chemical skeleton. Preferred are, when mixed with the polyisobutylene, those not impairing the transdermal absorption of the drug, and even more preferred are those enhancing the transdermal absorption. Preferred examples of such silicon-containing polymers are those having an organopolysiloxane skeleton or compositions containing such a polymer. The latter compositions are more preferred.

When a polymer having an organopolysiloxane skeleton has a hydroxyl groups (e.g., silanol group), at least one of the hydroxyl groups is preferably capped by a trimethylsilyl group. Further, the above composition should be adhesive. The capping by a trimethylsilyl group encompasses a form in which the terminal silanol group of the polymer having an organopolysiloxane skeleton is end-capped by a trimethylsilyl group.

Examples of the polymer having an organopolysiloxane skeleton include polydimethylsiloxane (polymers, etc., indicated as MQ in accordance with ASTMD-1418), polymethylvinyl siloxane (polymers, etc., indicated as VMQ in accordance with ASTMD-1418), polymethylphenyl siloxane (polymers, etc., indicated as PVMQ in accordance with ASMD-1418), etc.

Preferred compositions containing the polymer having an organopolysiloxane skeleton are those known as silicone pressure-sensitive adhesives. Examples of such a composition include those containing a silicone crude rubber, such as polydimethylsiloxane polymer, polymethylvinylsiloxane, polymethylphenylsiloxane, etc., and an MQ resin (three dimensionally-structured silicone resins composed of an "M unit" such as $(CH_3)_2SiO_{1/2}$, etc., and a "Q unit" such as $SiO_2$, etc.).

Usable compositions containing the polydimethylsiloxane polymer (and/or polymethylphenyl siloxane) and MQ resin are those into which a crosslinkage, such as $2SiCH_3 \rightarrow Si-CH_2-CH_2-Si$, is introduced using a crosslinking agent comprising an organic peroxide. Usable compositions containing the polymethylvinyl siloxane and MQ resin are those in which hydrosilylization reaction undergoes using a crosslinking agent having an SiH group. When mixing the silicone crude rubber and MQ resin described above, the terminal silanol group of the silicone crude rubber and the silanol group in the MQ resin may be dehydrated and condensed using, for example, an alkaline catalyst.

Examples of the composition containing a polymer having an organopolysiloxane skeleton in which at least one of the hydroxyl groups is capped by a trimethylsilyl group include pressure sensitive adhesives produced by Dow Corning (BIO-PSA 7-4101, BIO-PSA 7-4102, BIO-PSA 7-4103, BIO-PSA 7-4201, BIO-PSA 7-4202, BIO-PSA 7-4203, BIO-PSA 7-4301, BIO-PSA 7-4302, BIO-PSA7-4303), etc. Among these, Dow Corning BIO-PSA7-4102, a pressure sensitive adhesive, is particularly preferred. Such a silicon-containing polymer may be used singly or two or more may be used by mixing.

The mass ratio of the polyisobutylene to silicon-containing polymer in the drug layer is 20:1 to 7:3. When the polyisobutylene and the silicon-containing polymer are provided in the form of containing a volatile ingredient such as organic solvents, etc., the above mass ratio is calculated by deducting the volatile ingredient. When the silicon-containing polymer is a composition, the whole mass of the composition is used. With the mass ratio of the polyisobutylene to the silicon-containing polymer within the above range, a patch preparation sufficiently prevented from the sticking-out and crystal formation and having good drug permeability through the skin can be obtained. In view of the prevention of crystal formation and drug permeability through the skin of the patch preparation, the mass ratio of the polyisobutylene to the silicon-containing polymer in the drug layer is preferably 15:1 to 6:1, and more preferably 10:1 to 8:1.

It is preferred that the adhesive base used in the patch preparation of the present invention be substantially free of water. The term "substantially" used herein means that the manufacturing process does not include the step in which water is intentionally added to the adhesive base. It does not exclude the moisture contained in raw materials or moisture such as sweat or the like absorbed by the pressure-sensitive adhesive while the patch preparation is applied to the skin.

The pressure-sensitive adhesive of the present invention may contain a transdermal absorption enhancer. The transdermal absorption enhancer may be one or more compounds that exhibit the action of promoting transdermal absorption of the drug, and examples include fatty acids having a 6 to 20-carbon chain, aliphatic alcohols, fatty acid esters, alkyl ethers, aromatic organic acids, aromatic alcohols, aromatic organic esters, and aryl ethers. Further examples include lactate esters, acetate esters, monoterpene-based compounds, sesquiterpene-based compounds, Azone or derivatives thereof, glycerol fatty acid esters, sorbitan fatty acid esters, polysorbates, polyethylene glycol fatty acid esters, polyoxyethylene hydrogenated castor oils, sucrose fatty acid esters, and the like.

More specifically preferred examples of the transdermal absorption enhancer include caprylic acid, capric acid, caproic acid, lauric acid, myristic acid, palmitic acid, stearic acid, oleic acid, linoleic acid, linolenic acid, lauryl alcohol, myristyl alcohol, oleyl alcohol, cetyl alcohol, octyldodecanol, methyl laurate, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, ethyl acetate, propyl acetate, isopropyl palmitate, sorbitan monooleate, geraniol, thymol, eugenol, terpineol, l-menthol, borneol, d-limonene, isoeugenol, isoborneol, nerol, dl-camphor, glycerine monolaurate, glycerol monooleate, sorbitan monolaurate, sucrose monolaurate, polysorbate 20, polyethylene glycol monolaurate, polyethylene glycol monostearate, HCO-60 (hydrogenated castor oil), and 1-[2-(decylthio)ethyl]azacyclopentan-2-one, with fatty acid ester and aliphatic alcohols being particularly preferred. Among these, preferred are isopropyl myristate, isopropyl palmitate, sorbitan monooleate, octyldodecanol, and oleyl alcohol.

The content of the transdermal absorption enhancer in the drug layer is preferably 0.01 to 20%, more preferably 0.1 to 15 mass %, and further preferably 0.5 to 10%, based on the whole mass of the drug layer. When the content of the transdermal absorption enhancer in the drug layer exceeds 20%, skin irritations such as redness, blisters, and/or the like may be caused. When the content is less than 0.01%, the benefit from the addition of the transdermal absorption enhancer may not be attained.

The patch preparation of the present invention may further contain, if necessary, a hydrophilic polymer to allow the patch preparation to absorb sweat and like fluids secreted from the skin. Preferable examples of the hydrophilic polymer include light anhydrous silicic acid, cellulose derivatives (carboxymethylcellulose (CMC), sodium carboxymethylcellulose (CMCNa), methylcellulose (MC), hydroxypropylmethylcellulose (HPMC), hydroxypropylcellulose (HPC), hydroxyethylcellulose (HEC)), starch derivatives (pullulan), polyvinyl alcohol (PVA), polyvinyl pyrrolidone (PVP), polyvinyl acetate (VA), carboxyvinyl polymer (CVP), ethylene-vinyl acetate copolymer (EVA), Eudragit, gelatin, polyacrylic acids, polyacrylic acid soda, polyisobutylene-maleic anhydride copolymer, alginic acid, sodium alginate, carragheenan, gum arabic, tragacanth, karaya gum, and polyvinyl methacrylates, with light anhydrous silicic acid, cellulose derivatives (CMCNa, HPMC, HPC, MC and Eudragit being particularly preferred. The content of the hydrophilic polymer is preferably 0.1 to 20%, and particularly preferably 0.5 to 10%, based on the whole mass of the drug layer.

The patch preparation of the present invention can contain, as necessary, antioxidants, filling agents, crosslinking agents, preservatives, melting point depressing agents, ultraviolet absorbers, and mineral oils. Examples of the antioxidant include tocopherol and ester derivatives thereof, ascorbic acid, ascorbyl stearate, nordihydroguaiaretic acid, dibutylhydroxytoluene (BHT), butyl hydroxyanisol, etc.

Desirable Examples of the filling agent include talc, kaolin, water silica, light anhydrous silicic acid, aluminum hydroxide, calcium carbonate, magnesium carbonate, silicate (e.g., aluminum silicate, magnesium silicate, etc.), silicic acid, barium sulfate, calcium sulfate, calcium zincate, zinc oxide, titanium oxide, etc.

Desirable Examples of the crosslinking agent include thermosetting resins such as amino resins, phenol resins, epoxy resins, alkyd resins, unsaturated polyesters, etc. isocyanate compounds, block isocyanate compounds, organic crosslinking agents, and inorganic crosslinking agents such as metals or metal compounds.

Desirable examples of the preservative include disodium edetate, tetrasodium edetate, ethyl p-hydroxybenzoate, propyl p-hydroxybenzoate, butyl p-hydroxybenzoate, etc. Desirable melting point depressing agents are acetic acid, propionic acid, butyric acid, lactic acid, benzoic acid, and salicylic acid.

Preferable examples of the ultraviolet absorber are p-aminobenzoic acid derivatives, anthranilic acid derivatives, salicylic acid derivatives, cumarin derivatives, amino acid based compounds, imidazoline derivatives, pyrimidine derivatives, dioxane derivatives, etc. Preferred mineral oil is liquid paraffin.

These antioxidants, filling agents, crosslinking agents, preservatives, melting point depressing agents, ultraviolet absorbers, and mineral oils can be contained in a total proportion of preferably 30% or less, more preferably 20% or less, and particularly preferably 10% or less, based on the whole mass of the drug layer.

The patch preparation of the present invention can be manufactured by conventional methods such as solvent methods, hot melt method, or the like. For example, when a solvent method is employed for the manufacture, other ingredients are added to the organic solvent solution of the adhesive base to be contained, and the mixture is stirred, spread on the backing layer, and dried to form a drug layer, whereby the patch preparation of the present invention is obtained. Alternatively, when the adhesive base to be contained is applicable by a hot melt method, the adhesive base is dissolved at a high temperature, other ingredients are added thereto, the mixture is stirred and spread on the backing layer to form a drug layer, whereby the patch preparation of the present invention is obtained.

The patch preparation of the present invention can also be obtained by forming a drug layer using, in place of the backing layer, a release liner to be described later, and attaching a backing layer to the drug layer.

Further, the patch preparation of the present invention is not limited in other layers or ingredients constituting the layers insofar as the patch preparation is provided with the drug layer comprising such a pressure-sensitive adhesive described above and a backing layer supporting the drug layer. For example, the patch preparation of the present invention can contain, in addition to a backing layer and a drug layer, a release liner provided on the drug layer.

The backing layer is not limited, and preferred usable examples include cloth, nonwoven fabric, polyurethane, polyester, polyvinyl acetate, polyvinylidene chloride, polyethylene, polyethylene terephthalate, polybutylene terephthalate, paper, aluminum sheets, or composite materials thereof.

The release liner is not limited as far as it has good release from the drug layer, and preferred usable examples include a polyethylene terephthalate (PET) film, polyethylene film, polypropylene film, polytetrafluoroethylene film, etc.

According to the patch preparation of the present invention, an active drug dosage can also be easily adjusted in accordance with symptoms, age, body weight, sex, etc., of a patient by cutting, or the like, the patch preparation. According to the patch preparation of the present invention, the area of the drug layer to be contacted with the skin is not limited, but preferably 5 to 50 $cm^2$, more preferably 5 to 30 $cm^2$, and further preferably 5 to 10 $cm^2$. When the area of the patch preparation drug layer to be contacted with the skin is 50 $cm^2$ or less, the patch preparation is conveniently handled when applied, whereas when the area is 5 $cm^2$ or more, sufficient skin permeability of the drug can be easily maintained.

EXAMPLES

The present invention will be further described in detail with reference to examples, but the patch preparation of the present invention is not limited thereto.

Example 1

A high molecular weight polyisobutylene (Vistanex MM L-100, product of Exxon Mobil) having a viscosity average molecular weight of 1,200,000 and a low molecular weight polyisobutylene (Oppanol B11, product of BASF) having a viscosity average molecular weight of 35,000 were dissolved in toluene, and a composition containing a polymer having an organopolysiloxane skeleton BIO-PSA•7-4102 (silicone pressure-sensitive adhesive) was added thereto to prepare an adhesive base solution. An active drug comprising fentanyl and other ingredients comprising isopropyl myristate and oleyl alcohol were stirred at room temperature, the above adhesive base solution was added thereto, and the mixture was stirred to prepare a pressure-sensitive adhesive solution. The thus obtained pressure-sensitive adhesive solution was applied to a polyethylene terephthalate (PET) film treated with fluorocarbon (release liner), and subsequently dried to form a drug layer having a thickness of 90 μm. A PET film, i.e., a backing layer of 76.2 μm-thickness, was attached onto the drug layer to obtain the patch preparation of the present invention. The mass ratio of each ingredient is shown in Table 1.

Examples 2 to 5

The patch preparations of Examples 2 to 5 were manufactured in the same manner as in Example 1, provided that the mass ratios of the adhesive bases, active drugs, and other ingredients were as shown in Table 1.

TABLE 1

|  |  | Ex. 1 | Ex. 2 | Ex. 3 | Ex. 4 | Ex. 5 |
|---|---|---|---|---|---|---|
| Adhesive base | High molecular weight polyisobutylene (Vistanex MM L-100) | 18 | 17 | 9.5 | 11.8 | 12 |
|  | Low molecular weight polyisobutylene (Oppanol B11) | 72 | 68 | 56.5 | 70.7 | 74 |
|  | Silicone pressure-sensitive adhesive | 4.5 | 9.5 | 28.4 | 9.0 | 4.4 |
| Active drug | Fentanyl | 2.5 | 2.5 | 2.5 | — | — |
|  | Fentanyl citrate | — | — | — | 2.5 | 2.5 |
| Other ingredients | Isopropyl myristate | 2.0 | 3.0 | 3.0 | — | 6.0 |
|  | Cetyl palmitate | — | — | — | 2.0 | — |
|  | Oleyl alcohol | 1.0 | — | — | — | — |
|  | Liquid paraffin | — | — | — | 4.0 | — |
|  | CMC-Na | — | — | 1.0 | — | 1.0 |
|  | BHT | — | — | 0.1 | — | 0.1 |
|  | Total | 100.0 | 100.0 | 100.0 | 100.0 | 100.0 |
|  | Polyisobutylene/ silicone pressure sensitive adhesive | 20/1 | 9/1 | 7/3 | 9/1 | 20/1 |

Comparative Examples 1 to 8

The patch preparations of Comparative Examples 1 to 8 were manufactured in the same manner as in Example 1, provided that the mass ratios of the adhesive bases, active drugs and other ingredients were as shown in Table 2. For Comparative Examples 5 to 7, the pressure-sensitive adhesive solutions did not mix, making it difficult to manufacture the patch preparations. For this reason, these patch preparations were not eligible for the following evaluations.

[Evaluation of Patch Preparation]

The patch preparations manufactured in Examples 1 to 3, and Comparative Examples 1 to 4 and 8 described above were evaluated for the skin permeability, adhesiveness, stability over time, and crystal formation over time in accordance with the following test methods.

(Skin Permeation Test)

First, the dorsal skin of a hairless mouse was extirpated and mounted, with the dermal side against a receptor layer side, on a flow-through cell in which warm water of 33° C. was circulated around the outer part. Then, each patch preparation (application area of the drug layer: 5 cm$^2$) of Examples 1 to 3 and Comparative Examples 1 to 4 and 8 was applied to the stratum corneum side of the skin, and sampling for the receptor solution was carried out at every one hour for 12 hours at a rate of 10 ml/hr using saline as the receptor layer, whereby the flow amount was measured, and the drug concentration was also measured by a high-performance liquid chromatography. The drug permeation rate per hour was calculated from the measured values to determine the drug permeation rate per unit area of the skin at a steady state. The skin permeation rates of the drug over time from the start of the test are shown in Table 1, and the maximum values of the skin permeation rate of the drug (maximum skin permeation rate) obtained during 12 hours are shown in Table 3.

(Adhesion Test)

Each patch preparation of Examples 1 to 3 and Comparative Examples 1 to 4 and 8 was cut into a circular sheet sample of 25 mm in diameter, a release liner was peeled, and the drug layer was applied to a Bakelite plate for sensory analysis of the adhesion. The results obtained are shown in Table 3. The evaluation criteria for adhesion are shown below.

A: Exhibited good adhesion
B: Exhibited adhesion but easily peeled
C: Exhibited no adhesion (Stability Test for Long Term Storage)

Each patch preparation of Examples 1 to 3 and Comparative Examples 1 to 4 and 8 was packaged in a cellonium packaging material, and the package was sealed and stored at 25° C. for 1 month to evaluate over-time stability (sticking-out: a part of a drug (base) protrudes from between a backing layer and base. The results obtained are shown in Table 3. The evaluation criteria for stability are shown below.

TABLE 2

|  |  | Com. Ex. 1 | Com. Ex. 2 | Com. Ex. 3 | Com. Ex. 4 | Com. Ex. 5 | Com. Ex. 6 | Com. Ex. 7 | Com. Ex. 8 |
|---|---|---|---|---|---|---|---|---|---|
| Adhesive base | High molecular weight polyisobutylene (Vistanex MM L-100) | 19 | 18 | 18.2 | 18.3 | 6.5 | 3.9 | 0.95 | — |
|  | Low molecular weight polyisobutylene (Oppanol B11) | 75.5 | 71.5 | 72.5 | 73.2 | 39.5 | 23.5 | 8.45 | — |
|  | Silicone pressure-sensitive adhesive | — | — | 1.8 | 3.0 | 46.0 | 65.0 | 85.1 | 93.4 |
| Active drug | Fentanyl | 2.5 | — | 2.5 | 2.5 | — | 2.5 | 2.5 | — |
|  | Fentanyl citrate | — | 2.5 | — | — | 2.5 | — | — | 2.5 |
| Other ingredients | Isopropyl myristate | 2.0 | — | 3.0 | 3.0 | — | 3.0 | 3.0 | 3.0 |
|  | Cetyl palmitate | — | 3.0 | — | — | 3.0 | — | — | — |
|  | Oleyl alcohol | 1.0 | — | 2.0 | — | — | — | — | — |
|  | Liquid paraffin | — | 5.0 | — | — | 2.5 | — | — | — |
|  | CMC-Na | — | — | — | — | — | 2.0 | — | 1.0 |
|  | BHT | — | — | — | — | — | 0.1 | — | 0.1 |
|  | Total | 100.0 | 100.0 | 100.0 | 100.0 | 100.0 | 100.0 | 100.0 | 100.0 |
|  | Polyisobutylene/silicone pressure-sensitive adhesive | Polyisobutylene only | Polyisobutylene only | 50/1 | 30/1 | 5/5 | 3/7 | 1/9 | Silicone only |

A: Observed no sticking-out, easy to take out of a package
B: Observed slight sticking-out, not easy to take out of a package
C: Observed sticking-out, hard to take out of a package
(Crystal Formation Test for Long Term Storage)

Each patch preparation of Examples 1 to 3 and Comparative Examples 1 to 4 and 8 are packaged in a cellonium packaging material, and the package was sealed and stored at 25° C. for a month for visual inspection of the crystal formation. The results obtained are shown in Table 3. The evaluation criteria for crystal formation are shown below.

A: Observed no crystal formation after stored at 25° C. for 1 month
B: Observed crystal formation after stored at 25° C. for 1 month

TABLE 3

| | Ex. 1 | Ex. 2 | Ex. 3 | Com. Ex. 1 | Com. Ex. 2 | Com. Ex. 3 | Com. Ex. 4 | Com. Ex. 8 |
|---|---|---|---|---|---|---|---|---|
| Maximum transdermal permeation rate ($\mu g/cm^2/hr$) | 4.65 | 5.85 | 7.91 | 4.77 | 5.67 | 5.48 | 5.73 | 8.49 |
| Adhesion | A | A | B | B | A | A | A | C |
| Stability | A | A | A | C | C | C | B | A |
| Crystal formation | A | A | A | A | B | A | A | B |

The invention claimed is:

1. A patch preparation, comprising:
   a drug layer laminated on a backing layer, the drug layer consisting of a pressure-sensitive adhesive that comprises
   polyisobutylene,
   a silicon-containing polymer, and
   at least one compound selected from the group consisting of fentanyl and a pharmaceutically acceptable salt of fentanyl,
   the polyisobutylene and the silicon-containing polymer being present in the pressure-sensitive adhesive in a mass ratio of from 20:1 to 7:3,
   wherein no crystal formation of the compound is observed upon visual inspection after storage for one month.

2. The patch preparation according to claim 1, wherein the polyisobutylene comprises a high molecular weight polyisobutylene having a viscosity average molecular weight of 800,000 to 1,600,000 and a low molecular weight polyisobutylene having a viscosity average molecular weight of 30,000 to 80,000.

3. The patch preparation according to claim 1, wherein the silicon-containing polymer comprises an organopolysiloxane skeleton or a composition comprising an organopolysiloxane.

4. The patch preparation according to claim 3, wherein the polymer comprises the organopolysiloxane skeleton, and the organopolysiloxane skeleton comprises one or more hydroxyl groups and at least one of the one or more hydroxyl groups is capped by a trimethylsilyl group.

5. The patch preparation according to claim 3, wherein the organopolysiloxane skeleton is a polydimethylsiloxane skeleton.

6. The patch preparation according to claim 3, wherein the composition is a pressure-sensitive composition.

7. The patch preparation according to claim 1, wherein the pressure-sensitive adhesive further comprises a transdermal absorption enhancer.

8. The patch preparation according to claim 7, wherein the transdermal absorption enhancer comprises at least one compound selected from the group consisting of isopropyl myristate, isopropyl palmitate, sorbitan monooleate, oleyl alcohol, propylene glycol, dipropylene glycol and octyl dodecanol.

9. The patch preparation according to claim 1, wherein the drug layer comprises a skin contact area of from 5 to 50 $cm^2$.

10. The patch preparation according to claim 1, wherein the drug layer further comprises isopropyl myristate.

11. The patch preparation according to claim 10, wherein
    the mass ratio of the polyisobutylene to the silicon-containing polymer is in a range of from 10:1 to 8:1,
    the fentanyl or the pharmaceutically acceptable salt of fentanyl is present in an amount of from 1 to 6% by mass of the drug layer,
    the isopropyl myristate is present in an amount of from by 0.5 to 10% by mass of the drug layer, and
    the polyisobutylene being present in an amount of 50 to 90% by mass of the drug layer and comprises a high molecular weight polyisobutylene and a low molecular polyisobutylene having mass ratio of high molecular weight polyisobutylene to low molecular polyisobutylene in a range of from 1:9 to 2:3.

12. The preparation according to claim 11, wherein the high molecular weight polyisobutylene has a viscosity average molecular weight of 800,000 to 1,600,000 and the low molecular weight polyisobutylene has a viscosity average molecular weight of 30,000 to 80,000.

13. The patch preparation according to claim 11, wherein the silicon-containing polymer comprises an organopolysiloxane skeleton or a composition comprising an organopolysiloxane.

14. The patch preparation according to claim 13, wherein the polymer comprises the organopolysiloxane skeleton, and the organopolysiloxane skeleton comprises one or more hydroxyl groups and at least one of the one or more hydroxyl groups is capped by a trimethylsilyl group.

15. The patch preparation according to claim 13, wherein the organopolysiloxane skeleton is a polydimethylsiloxane skeleton.

* * * * *

UNITED STATES PATENT AND TRADEMARK OFFICE
CERTIFICATE OF CORRECTION

PATENT NO. : 8,647,664 B2  
APPLICATION NO. : 12/309226  
DATED : February 11, 2014  
INVENTOR(S) : Honma et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 694 days.

Signed and Sealed this

Twenty-ninth Day of September, 2015

Michelle K. Lee
*Director of the United States Patent and Trademark Office*